US007231826B2

(12) United States Patent
Bossi et al.

(10) Patent No.: US 7,231,826 B2
(45) Date of Patent: *Jun. 19, 2007

(54) NON-DESTRUCTIVE INSPECTION DEVICE FOR INSPECTING LIMITED-ACCESS FEATURES OF A STRUCTURE

(75) Inventors: Richard H. Bossi, Renton, WA (US); Gary E. Georgeson, Federal Way, WA (US); James C. Kennedy, Renton, WA (US)

(73) Assignee: The Boeing Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/752,890

(22) Filed: Jan. 7, 2004

(65) Prior Publication Data

US 2005/0145033 A1 Jul. 7, 2005
US 2006/0010980 A9 Jan. 19, 2006

Related U.S. Application Data

(63) Continuation-in-part of application No. 10/620,464, filed on Jul. 16, 2003, now Pat. No. 6,722,202.

(51) Int. Cl.
*G01N 29/24* (2006.01)
(52) U.S. Cl. .............................. 73/618; 73/620; 73/633; 73/866.5
(58) Field of Classification Search ................. 73/618, 73/620, 623, 624, 633, 635, 866.5; 356/241.1
See application file for complete search history.

(56) References Cited

U.S. PATENT DOCUMENTS

| 4,010,636 A | 3/1977 | Clark et al. |
| 4,398,424 A | 8/1983 | Abts |
| 4,399,703 A | 8/1983 | Matzuk |
| 4,848,159 A * | 7/1989 | Kennedy et al. .............. 73/641 |
| 5,062,301 A | 11/1991 | Aleshin et al. |
| 5,343,750 A * | 9/1994 | Bashyam ..................... 73/635 |
| 5,741,973 A | 4/1998 | Clark et al. |
| 6,180,928 B1 | 1/2001 | Garrigus |
| 6,722,202 B1 * | 4/2004 | Kennedy et al. .............. 73/634 |

FOREIGN PATENT DOCUMENTS

| GB | 2 198 532 A | 6/1988 |
| JP | 61230056 A | 10/1986 |

\* cited by examiner

*Primary Examiner*—John E. Chapman
(74) *Attorney, Agent, or Firm*—Alston & Bird LLP

(57) ABSTRACT

There is provided a non-destructive inspection device having an actuating portion and at least one inspecting portion. The inspecting portion(s) are magnetically coupled to the actuating portion so that the inspecting portion(s) may be moved into limited-access areas to inspect features of a structure. The inspecting portion(s) each include at least one inspection sensor that transmits and/or receives signals that, when processed, indicate defects in the features of the structure. The actuating portion may include a handle for manual movement of the inspection device, or alternatively may include a motorized drive wheel for motorized positioning of the inspection device. A positional encoder device, such as an encoder wheel or optical encoder, may also be included in the actuating portion or inspecting portion(s) to monitor the location of the inspection device for more accurate or informative inspection results.

22 Claims, 6 Drawing Sheets

NON-DESTRUCTIVE INSPECTION DEVICE FOR INSPECTING LIMITED-ACCESS FEATURES OF A STRUCTURE

RELATED APPLICATION DATA

This application is a continuation-in-part of U.S. application Ser. No. 10/620,464, filed Jul. 16, 2003 now U.S. Pat. No. 6,722,202.

FEDERALLY SPONSORED RESEARCH OR DEVELOPMENT

This invention was made with government support under Contract No. F33615-98-3-5103 awarded by the Department of the Air Force. The government may have certain rights in this invention.

FIELD OF THE INVENTION

The present invention relates generally to non-destructive inspection devices. More particularly the invention relates to an inspection device for inspecting limited-access features of a structure.

BACKGROUND OF THE INVENTION

Non-destructive inspection of structures involves thoroughly examining a structure without harming the structure or requiring significant disassembly of the structure. Non-destructive inspection is advantageous for many applications in which a thorough inspection of the exterior and/or interior of a structure is required. For example, non-destructive inspection is commonly utilized in the aircraft industry to inspect aircraft structures for any type of internal or external damage to the structure.

Among the structures that are routinely non-destructively inspected are composite structures. In this regard, composite structures are commonly used throughout industry because of their engineering qualities, design flexibility, and low weight. As such, it is frequently desirable to inspect composite structures to identify any flaws, such as cracks, voids, or porosity, which could adversely affect the performance of the composite structure.

Various types of sensors may be utilized to perform non-destructive inspection. One or more sensors may move over the structure to be examined, and receive data regarding the structure from which internal flaws can be identified. For example, a pulse-echo, thru-transmission, or shear wave sensor may be utilized to obtain ultrasonic data, such as thickness gauging, detection of laminar defects and porosity, and/or crack detection in the structure. Resonance, pulse echo, or mechanical impedance sensors may also be utilized to provide indications of voids or porosity, such as in adhesive bondlines of the structure. The data acquired by the sensors is typically processed by a processing element, and the processed data may be presented to a user via a display.

Accessibility to the features of the structure requiring inspection is one consideration in choosing a non-destructive inspection device. Access to the feature requiring inspection may be so limited that a manual inspection by a technician is not possible. An example of a structure with limited access is an internal joint of a wing structure. More specifically, the bondlines produced by close-out joints created when the last sections of the wing are attached exemplify the limited-access features of a structure.

Limited-access features of a structure, such as the close-out joints, are difficult to fully inspect using contemporary inspection devices. Accordingly, a need exists for a convenient and reliable non-destructive inspection device to inspect limited-access features of a structure.

BRIEF SUMMARY OF THE INVENTION

The invention addresses the above needs and achieves other advantages by providing a non-destructive inspection device for inspecting a feature of a structure, such as a limited-access feature. The inspection device includes an actuating portion and at least one inspecting portion that are magnetically coupled so that the inspecting portion moves in concert with the actuating portion. The inspecting portion includes an inspection sensor and at least one magnet. The actuating portion also includes at least one magnet so that when the actuating portion is placed on a first surface of the structure and the inspecting portion is positioned on a surface of the structure opposite the first surface, the two portions are magnetically coupled so that movement of the actuating portion causes the inspecting portion to move in concert with the actuating portion without the inspecting portion directly contacting the actuating portion. Thus, the inspecting portion can be moved to be proximate the feature of the structure to inspect the feature. The inspection device of one embodiment includes two inspecting portions, wherein one inspecting portion has an ultrasonic transmitter and the other inspecting portion has an ultrasonic receiver such that the transmitter and receiver are aligned to detect flaws in a feature of the structure that extends outwardly from the surface upon which the actuating portion and the inspecting portions are placed.

Additional embodiments of the present invention include an array of sensors on the inspecting portions and/or a plurality of magnets on each actuating portion and inspecting portions. A further embodiment includes a handle on the actuating portion for manual movement of the inspection device, while an alternative embodiment includes a motorized wheel for automated movement of the inspection device. In addition, the actuating portion or the inspecting portions may include a positional encoder device to monitor the position of the inspection device. Alternative inspection sensors may be used such as laser ultrasonic transducers or optical borescopes.

A method of inspecting a structure is also provided by the present invention. To inspect the structure, an actuating portion of a non-destructive inspection device is placed on a first surface of the structure and at least one inspecting portion of the non-destructive inspection device is positioned on a surface of the structure opposite the first surface. At least one magnet in the inspecting portion magnetically couples to at least one magnet in the actuating portion. The actuating portion is moved on the surface of the structure such that the inspecting portion is moved in concert with the actuating portion. The inspection sensor creates an output that can be monitored by the technician to find flaws or defects. Accordingly, the non-destructive inspection device and inspection method provide for convenient and reliable inspection of features of a structure.

BRIEF DESCRIPTION OF THE SEVERAL VIEWS OF THE DRAWINGS

Figure 1:
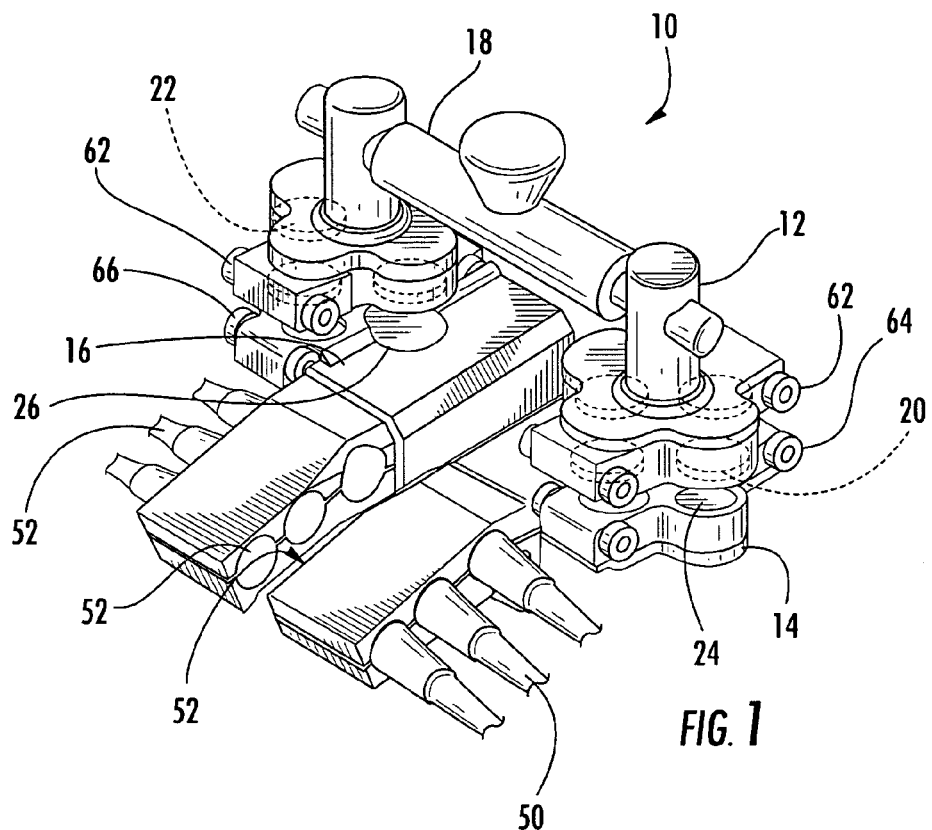
Figure 3:
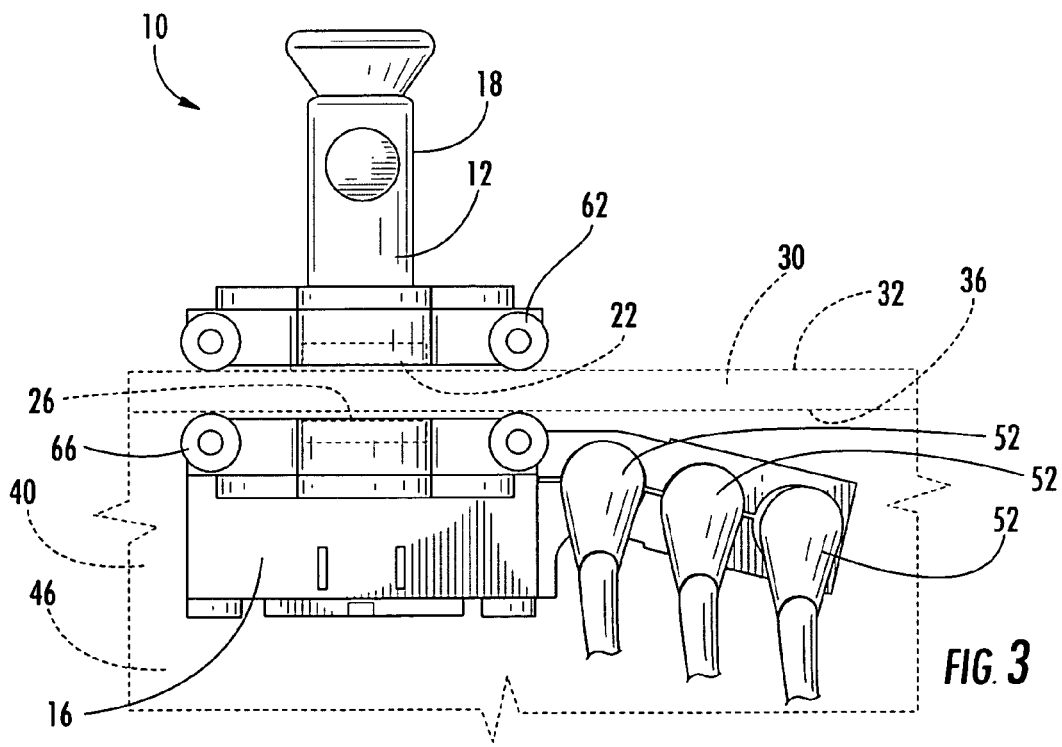
Figure 2:
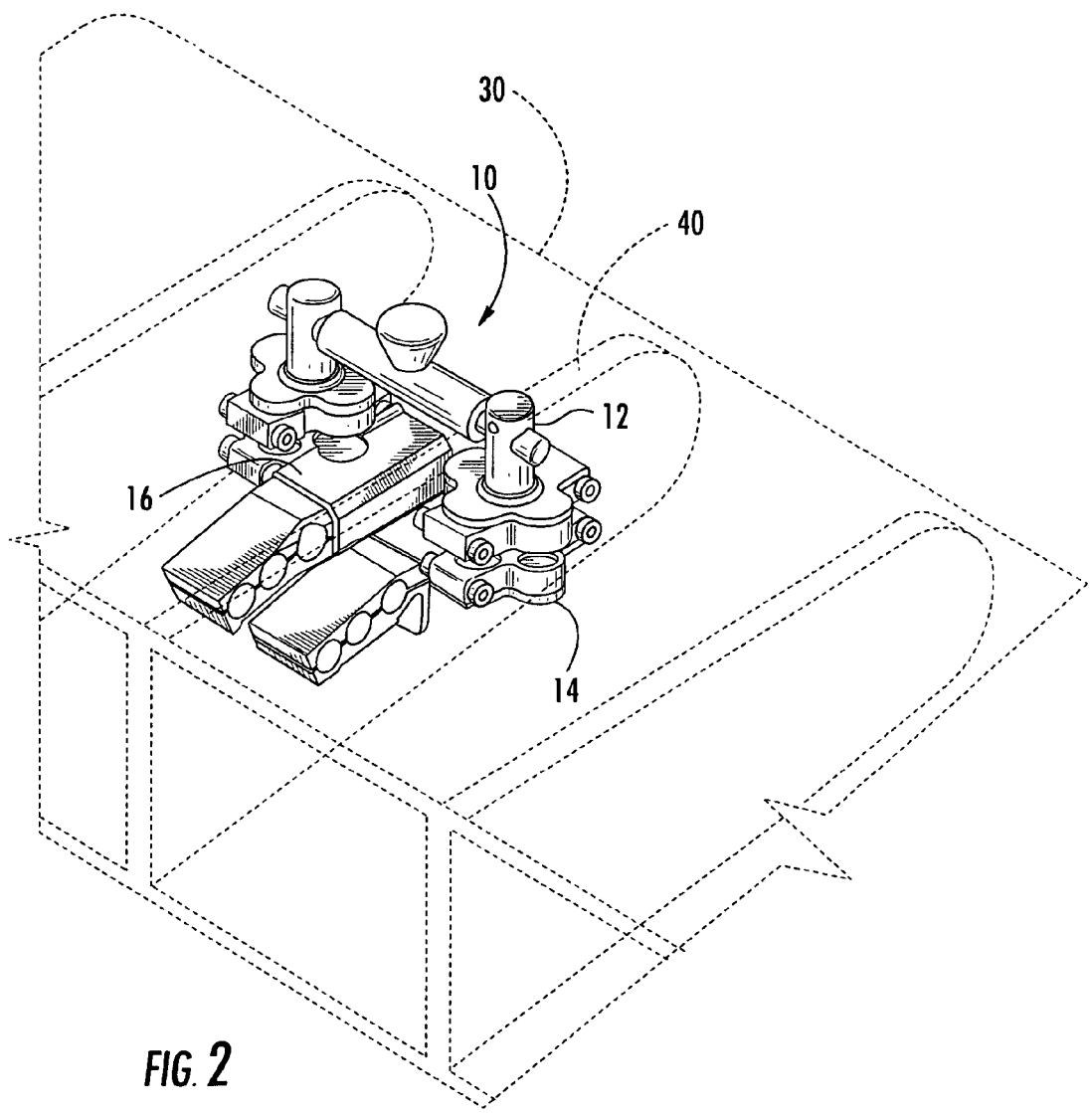
Figure 4:
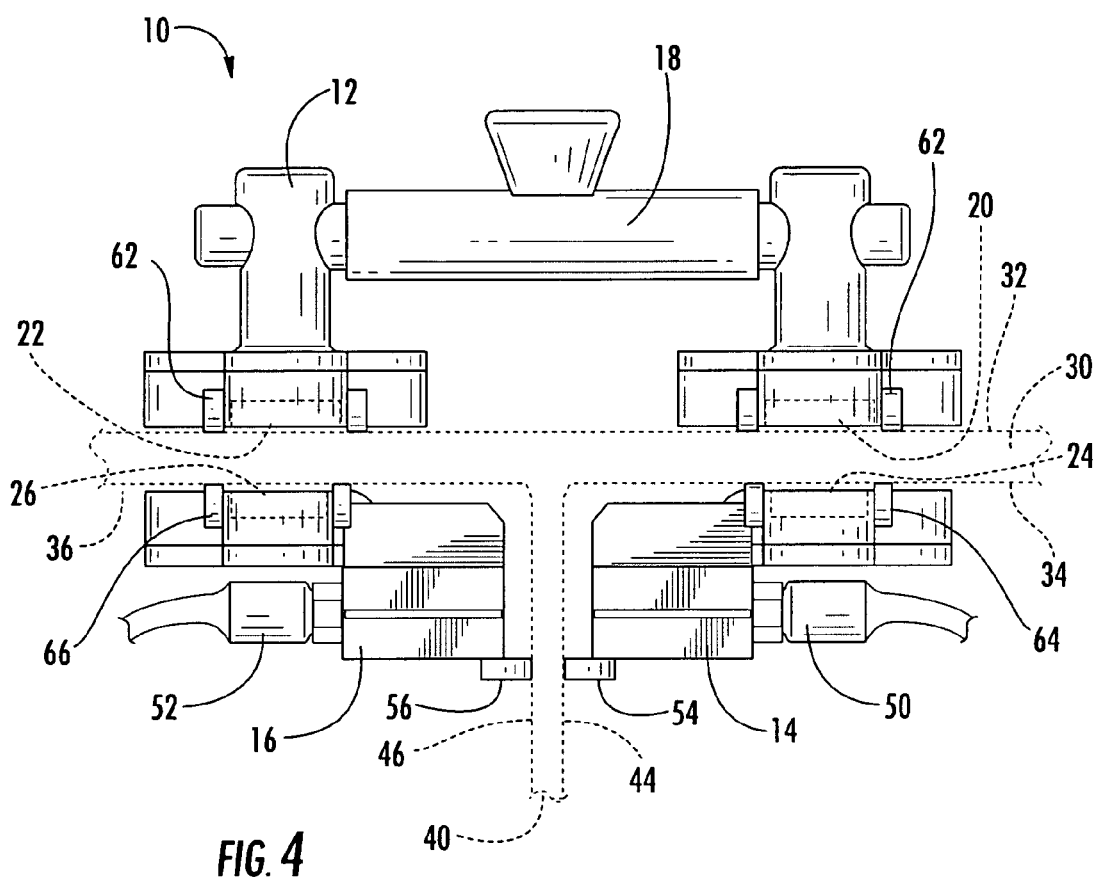
Figure 5:
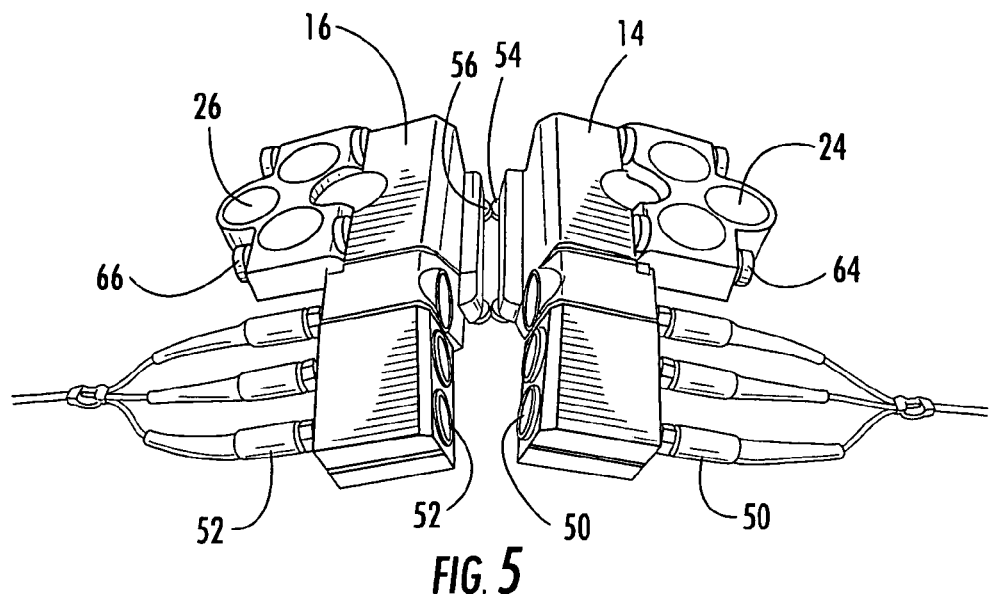
Figure 6:
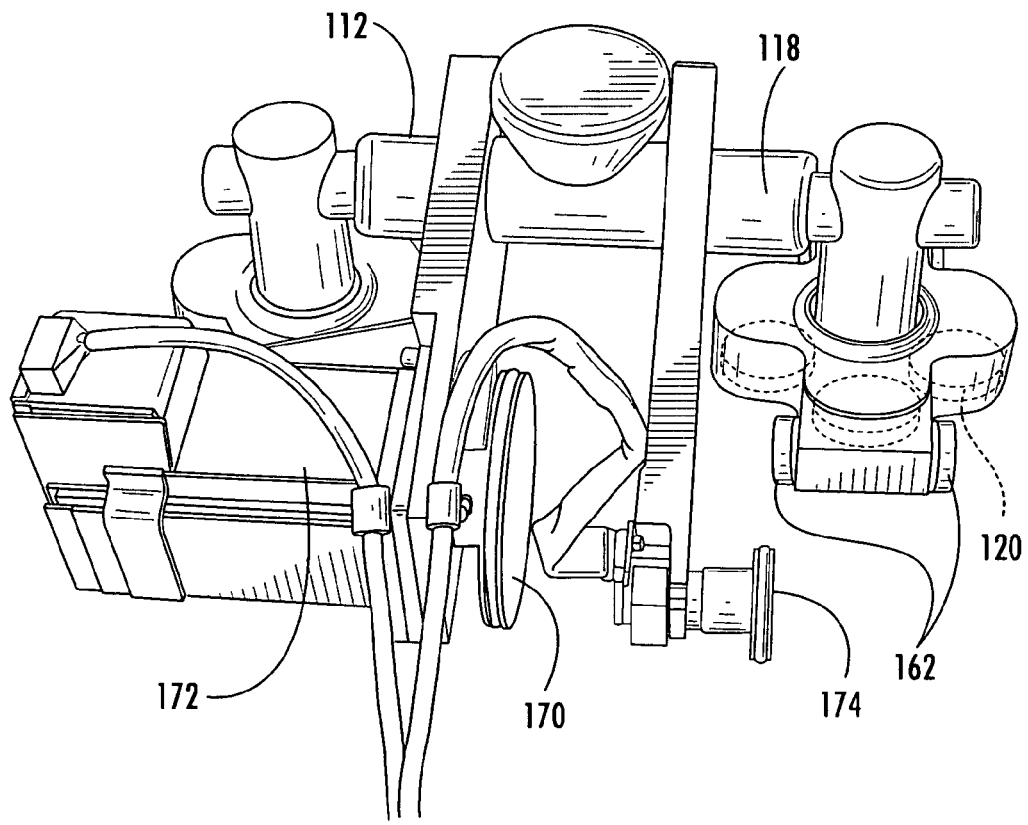
Figure 7:
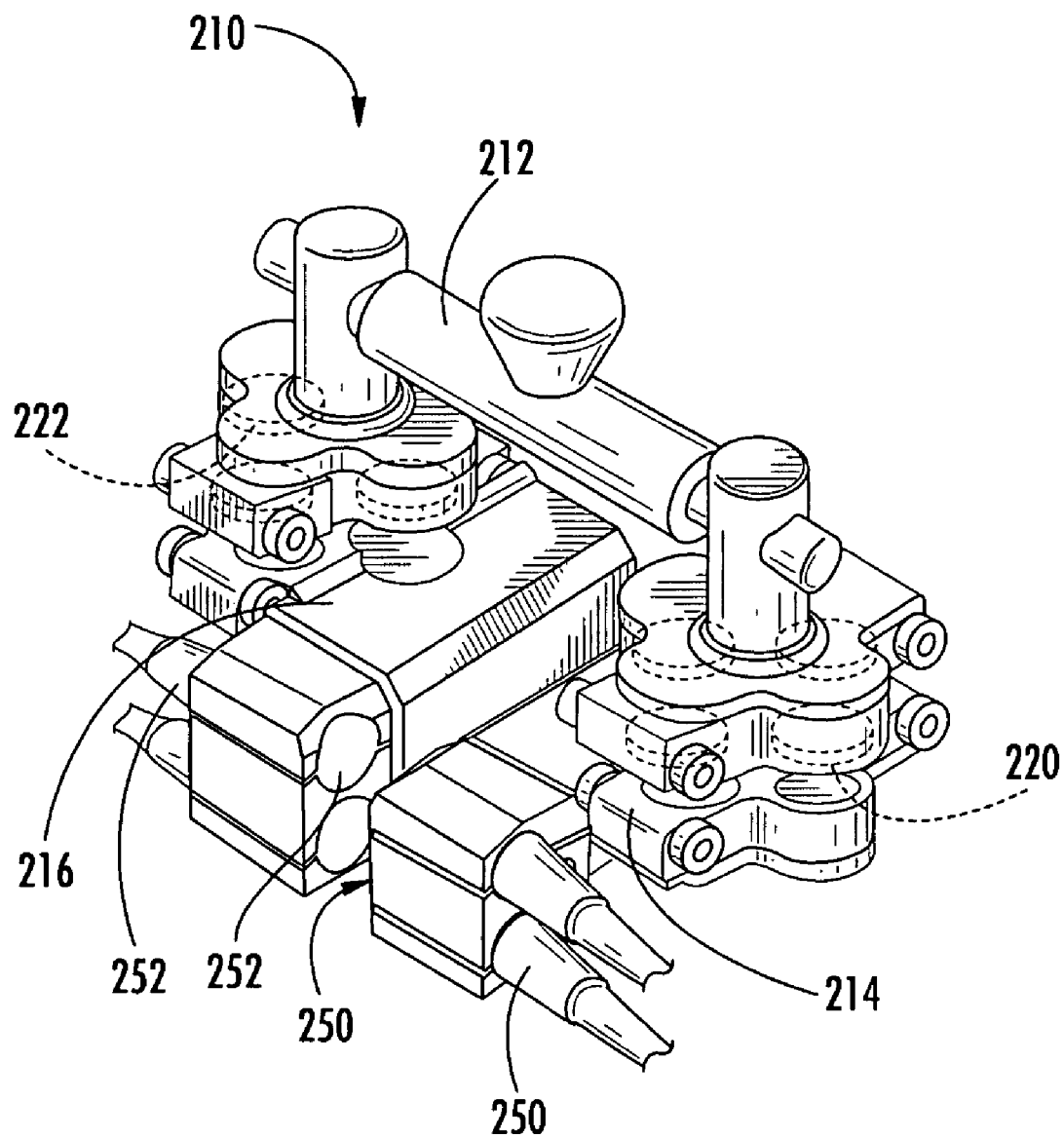
Figure 8:
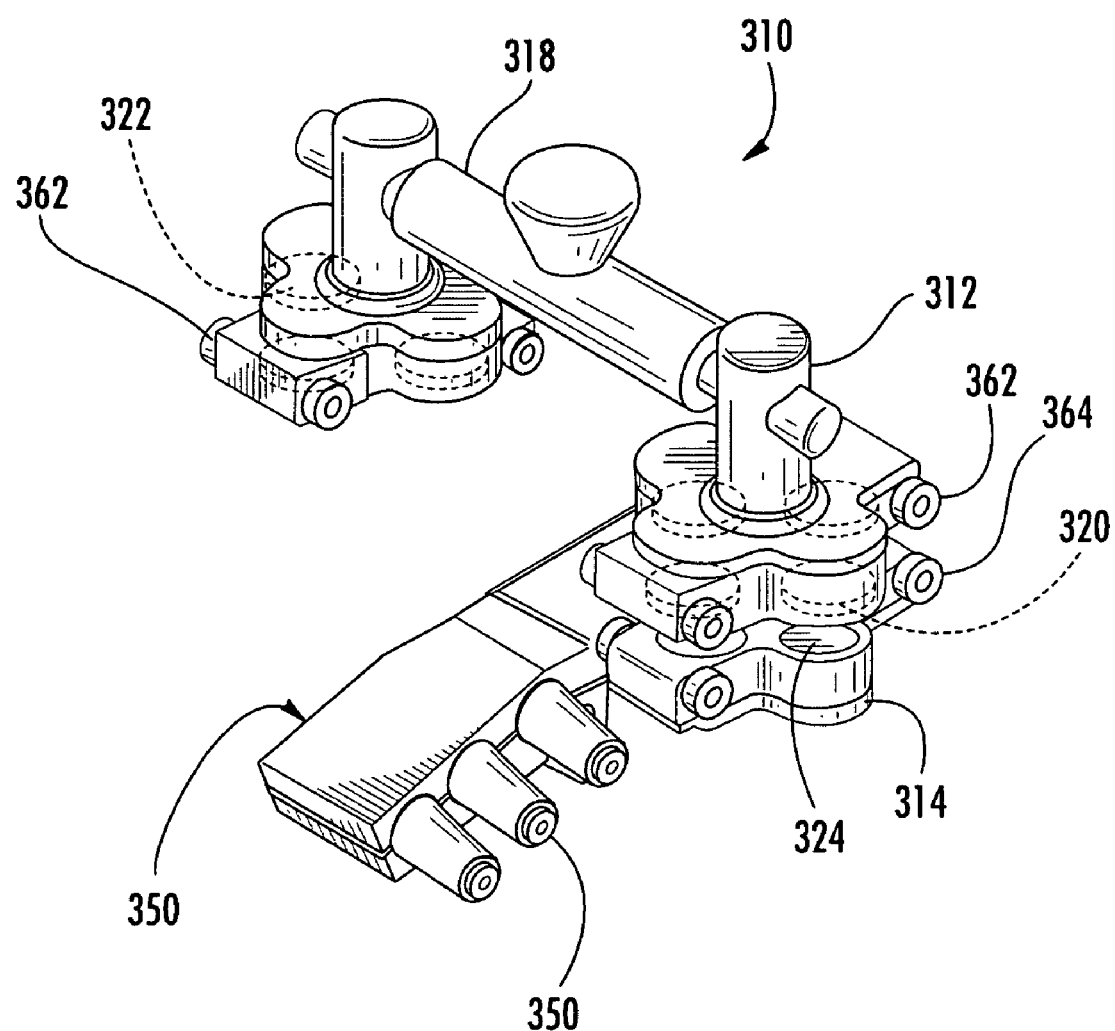

Having thus described the invention in general terms, reference will now be made to the accompanying drawings, which are not necessarily drawn to scale, and wherein:

FIG. 1 is a perspective view of a non-destructive inspection device in accordance with one embodiment of the present invention, illustrating an actuating portion and two inspecting portions;

FIG. 2 is an environmental view of the inspection device of FIG. 1, illustrating the inspection device positioned on a structure to inspect limited access features of the structure;

FIG. 3 is a side planar view of the inspection device of FIG. 1, illustrating the actuating portion on a first surface of a structure and one inspecting portion positioned on a surface opposite the first surface and suspended by the magnetic coupling between the actuating portion and the inspecting portion;

FIG. 4 is a rear planar view of the inspection device of FIG. 1, illustrating the actuating portion on a first surface of the structure and the two inspecting portions positioned on a surface opposite the first surface such that the feature of the structure to be inspected is located between the inspecting portions;

FIG. 5 is a top perspective view of the two inspecting portions of the inspection device of FIG. 1, illustrating the plurality of magnets and the array of inspection sensors on each inspecting portion;

FIG. 6 is a perspective view of an actuating portion of a non-destructive inspection device in accordance with a second embodiment of the present invention, illustrating an actuating portion that includes a motorized drive wheel and a positional encoder device;

FIG. 7 is a perspective view of a non-destructive inspection device in accordance with a third embodiment of the present invention, illustrating two inspecting portions having vertical arrays of inspection sensors; and FIG. 8 is a perspective view of a non-destructive inspection device in accordance with a fourth embodiment of the present invention, illustrating an inspection device with only one inspecting portion and with wireless inspection sensors.

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

With reference to FIGS. 1–5, a non-destructive inspection device 10 in accordance with one embodiment of the invention is illustrated. The non-destructive inspection device 10 includes an actuating portion 12, a first inspecting portion 14, and a second inspecting portion 16. The actuating portion 12 and the inspecting portions 14 and 16 are individual portions and are not directly connected in the illustrated embodiment. The actuating portion 12 is structured for placement on a surface of the structure undergoing inspection. The inspecting portions 14 and 16 are structured for positioning on a surface opposite the surface the actuating portion is placed.

The actuating portion 12 includes at least one magnet, and preferably includes a plurality of magnets, such as four magnets in the illustrated embodiment, for magnetically coupling with each of the inspecting portions 14 and 16. The magnetic coupling provides a remote connection between the actuating portion 12 and the inspecting portions 14 and 16 so that the inspecting portions move in concert with the actuating portion. The actuating portions 14 and 16 move in concert with the actuating portion 12 such that the actuating portions maintain substantially consistent positions relative to the actuating portion while the inspecting portions are magnetically coupled to the actuating portion. The actuating portion 12 of FIG. 1 also includes a handle 18 that connects a first plurality of magnets 20 to a second plurality of magnets 22. The first plurality of magnets 20 magnetically couple with a plurality of magnets 24 of the first inspecting portion 14 during operation of the inspection device 10. Likewise, the second plurality of magnets 22 of the actuating portion 12 magnetically couple with a plurality of magnets 26 of the second inspecting portion 16 during operation of the inspection device 10. The first plurality of magnets 20 are magnetically coupled to the plurality of magnets 24 of the first inspecting portion 14 when the actuating portion 12 and the first inspecting portion are positioned on opposite surfaces of a structure 30, as shown in FIG. 4. The magnets are advantageously positioned such that the magnets are proximate the opposed surfaces 32 and 34 of the structure 30 such that the magnetic coupling therebetween is maximized. Similarly, the second plurality of magnets 22 are magnetically coupled to the plurality of magnets 26 of the second inspecting portion 16 when the actuating portion 12 and the second inspecting portion are positioned on opposite surfaces of the structure 30, as also shown in FIG. 4. The magnets are advantageously positioned such that the magnets are proximate the opposed surfaces 32 and 36 of the structure 30 such that the magnetic coupling therebetween is maximized.

The magnets 20, 22, 24, and 26 of the illustrated embodiment, shown in FIGS. 1 and 5 are preferably pancake magnets formed of neodymium iron boron, which have advantageously greater magnetic flux (around 12,000 gauss) than standard ceramic or ferrite magnets (around 3,900 gauss). Although each plurality of magnets must comprise at least one magnet, the magnets of the illustrated embodiment are arranged in sets of four for a total of sixteen magnets included in the inspection device 10. Further embodiments of the invention may include magnets of different material, such as Samarium Cobalt or Alnico to list two non-limiting examples of alternative magnets, and/or may create the magnetic coupling with electromagnets or other magnetic coupling means. The present invention may further comprise magnetic shunting mechanisms to control the magnetic flux of the magnetic couplings, a non-limiting example being rare earth metal switched magnetic devices disclosed in U.S. Pat. No. 6,180,928 that is assigned to the present assignee.

Structures 30 that may be inspected with the inspection device 10 of the present invention may include but are not limited to composites, non-ferromagnetic metals (e.g. aluminum alloy, titanium alloy, or aluminum or titanium hybrid laminates such as GLARE or Ti/Gr), and polymers. It should be noted that the first surface 32, the surfaces 34 and 36, and the material therebetween, which collectively define the material through which the actuating portion 12 and the inspecting portions 14 and 16 are magnetically coupled, preferably comprise a non-ferromagnetic material because the magnetic coupling would be diminished or eliminated by a ferromagnetic material located between the actuating portion and the inspecting portions.

The pluralities of magnets support each inspecting portion 14 and 16 and keep each of the inspecting portions aligned. Each plurality of magnets 20, 22, 24, and 26 comprises at least one individual magnet and is not limited to four magnets each. Each plurality of magnets may also be arranged in any pattern, but the plurality of magnets that are to be aligned with and magnetically coupled to one another preferably have the same pattern for maximum coupling of the magnets.

Referring to FIGS. 2–4, the structure 30 includes a feature 40 that extends outwardly from the surfaces 34 and 36 of the structure, such as being perpendicular thereto. As shown in FIG. 2, the feature 40 of a structure 30 may be a limited-access feature such as a shear tie or spar that is bonded or fastened to the skin or joined to or protruding from the surfaces 34 and 36. The feature 40 may also include a pi joint connecting the feature to the surfaces 34 and 36, wherein the actual joint may be inspected by the inspection device 10. Alternative features to be inspected may be a feature of any shape, angular orientation, size, or location. The feature 40 of FIG. 4 represents an interior rib of a wing structure comprising a composite material for use in the aerospace industry; however, the feature 40 may represent any portion of any structure to be non-destructively inspected. Furthermore, the feature 40 may be of any material that may be non-destructively inspected, including ferromagnetic material. If no magnetic coupling is required through the feature 40 to be inspected, a structure 30 having a feature comprising a ferromagnetic material may be inspected if the material through which the actuating portion 12 and inspecting portions 14 and 16 are magnetically coupled comprises a non-ferromagnetic material. Such a structure 30 would typically be used for non-aerospace applications because of the importance of minimal weight in aerospace applications and a ferromagnetic feature 40 would usually be heavier than a non-ferromagnetic feature such as a composite feature. The inspection sensors used to inspect a ferromagnetic feature 40 preferably are impervious to the magnetic fields created by the magnetic couplings between the actuating portion and inspecting portions.

The feature 40 of the illustrated embodiment includes a first face 44 facing the first surface 34 and a second face 46 facing the second surface 36. When the inspection device 10 is positioned on the structure 30, as shown in FIG. 4, the feature 40 is located between the first inspecting portion 14 and the second inspecting portion 16. Further embodiments of the inspection device, such as the embodiment illustrated in FIG. 8, may include only one inspecting portion with at least one inspection sensor for non-destructive inspection of the feature 40, i.e., one-sided inspection relying on the reflection of signals from within the feature or viewing the feature with an optical borescope or miniature camera. One-sided ultrasonic inspection methods such as pitch catch, pulse echo, resonance, mechanic impedance, etc. are non-limiting examples of one-sided inspection techniques of further embodiments of the present invention comprising only one inspecting portion.

The first inspecting portion 14 and the second inspecting portion 16 of FIGS. 1–5 each include three inspection sensors. Further embodiments of the inspection device 10 may include any number of inspection sensors in various configurations. The first inspection sensors 50 of the first inspecting portion 14 are ultrasonic transmitters, while the second inspection sensors 52 of the second inspecting portion 16 are ultrasonic receivers. These inspection sensors 50 and 52 are advantageous because they do not require direct contact on the first face 44 and second face 46, respectively, of the feature 40 and do not require a couplant. Alternative embodiments of the present invention may include other non-contact inspection sensors such as fiber-optic laser ultrasonic systems, velocimetric or mechanical impedance analysis devices, optical borescopes, miniature cameras, infrared sensors, capacitive sensors, and x-ray sources and detectors, to list a few non-limiting examples of sensors not requiring a couplant. Inspection sensors requiring a couplant may also be used. Non-limiting examples include traditional contact pulse-echo and through-transmission ultrasonic transducers, as well as UT resonance probes. In one advantageous embodiment, an inspection sensor 50 and/or 52 that does not require a couplant is used because no clean-up or collection of a couplant is required, which may be very difficult because of the limited access to the feature being inspected.

For a structure 30 comprising a ferromagnetic material in the feature 40, but non-ferromagnetic material in the material through which the actuating portion 12 and inspecting portions 14 and 16 are magnetically coupled, as described above, the inspection sensor(s) may comprise eddy current inspection sensors to inspect the ferromagnetic feature. An example of such a structure is typically a non-aerospace application comprising ferromagnetic spars and non-ferromagnetic skins, as described above.

To maintain a predefined distance between the inspection sensors 50 and 52 and the first face 44 and second face 46, respectively, of the feature 40 and to facilitate movement of the inspecting portions 14 and 16, rollers 54 and 56 are provided on the first inspecting portion 14 and the second inspecting portion 16, respectively, as shown in FIG. 4. The rollers 54 of the illustrated embodiment are located near the first plurality of magnets 20; however, further embodiments of the inspection device 10 may include rollers located at any position on the first inspecting portion 14, such as near the first inspection sensors 50. Likewise the rollers 56 of the second inspecting portion 16 may be located at any position on the second inspecting portion, but preferably mirror the rollers 54 of the first inspecting portion 14, as shown in FIG. 5. The rollers 54 and 56 also help maintain the alignment of the inspecting portions 14 and 16, respectively. The inspecting portions 14 and 16 may, alternatively, include skids, skis, or the like for maintaining the predefined distance and for facilitating movement of the inspecting portions over the feature 40.

Operation of the inspection device 10 consists of placing the actuating portion 12 on a first surface 32 of the structure 30 and positioning at least one inspecting portion, such as the first inspecting portion 14, on a surface 34 opposite the first surface such that the inspecting portion is proximate the feature 40 to be inspected. The magnets 20 and 24 of each portion 12 and 14, respectively, magnetically couple the inspecting portion to the actuating portion such that the inspecting portion is supported and aligned. To non-destructively inspect the feature 40, the inspection sensor 50 of the inspecting portion 14 is activated such that the reflected signals received by the inspection sensor 50 are sent to a processing element for analysis and storage and, in one embodiment, for creating an output on a display that can be monitored by the technician. The displayed output, which may be data in any form such as numeric data or graphic data to list two non-limiting examples, advantageously represents the location and size of internal flaws or defects in the feature being inspected.

The actuating portion 12 is moved along the first surface 32 such that the inspecting portion 14 is correspondingly moved along the surface 34. The inspection device 10 of FIG. 1 may be manually moved by the technician who grasps the handle 18 to advance the actuating portion 12. The inspection device 10 is advanced along the length of the feature 40 to fully inspect the feature, such that the processed data is preferably collected for a summary of the overall inspection results to illustrate or indicate any flaws or defects in the inspected feature. After the feature 40 is sufficiently inspected, the inspection device 10 can be removed by pulling the first inspecting portion 14 from the structure 30 to overcome the magnetic couplings and then removing the actuating portion 12. Notably, the technician can inspect the feature 40 in a relatively blind manner since the technician generally does not need to access the surface 34 of the structure proximate the feature, other than to initially position the first inspecting portion 14 and to retrieve the first inspecting portion following the inspection.

The inspection device 10 may also be operated with two or more inspecting portions. The actuating portion 12 is placed on a first surface 32 of the structure 30, the first inspecting portion 14 is positioned on a surface 34 opposite the first surface, and the second inspecting portion 16 is positioned on a surface 36 that is also opposite the first surface such that the feature 40 to be inspected is located between the inspecting portions. The magnets of each portion magnetically couple the inspecting portions 14 and 16 to the actuating portion 12 such that the inspecting portions are supported by the actuating portion and aligned with the actuating portion. The inspecting portions 14 and 16 are also in generally fixed relative positions with respect to each other when each is magnetically coupled to the actuating portion 12. To non-destructively inspect the feature 40, the inspection sensors 50 and 52 of the inspecting portions 14 and 16, respectively, are activated such that the signals transmitted by the first inspection sensors 50 pass through the feature 40 and are received by the second inspection sensors 52 prior to being sent to a processing element for analysis and storage and, in one embodiment, for creating an output on a display that can be monitored by the technician. The actuating portion 12 is moved along the first surface 32 such that the inspecting portions 14 and 16 are correspondingly moved along the surfaces 34 and 36. The inspection device 10 of FIG. 1 may be manually moved by the technician who grasps the handle 18 to advance the actuating portion 12. The inspection device 10 is advanced along the length of the feature 40 to fully inspect the feature, such that the processed data is preferably collected for a summary of the overall inspection results to illustrate or indicate any flaws or defects in the inspected feature. After the feature 40 is sufficiently inspected, the inspection device 10 can be removed by pulling the inspecting portions 14 and 16 from the structure 30 to overcome the magnetic couplings and then removing the actuating portion 12. Similar to the inspection with one inspecting portion, the technician can inspect the feature 40 in a relatively blind manner since the technician generally does not need to access the surfaces 34 and 36 of the structure proximate the feature, other than to initially position the inspecting portions 14 and 16 and to retrieve the inspecting portions following the inspection.

A set of rollers 62, skids, skis, or the like may be provided on the actuating portion 12 to facilitate movement of the actuating portion and a set of rollers 64, skids, skis, or the like may be provided on the first inspecting portion 14 to facilitate movement along the surface 34. A set of rollers 66, skids, skis, or the like may also be included on the second inspecting portion 16 to facilitate movement along the surface 36. In the illustrated embodiment, the sets of rollers 62, 64, and 66 each include four individual rollers located near the plurality of magnets of each portion such that the magnets are nominally suspended above their respective surface, as shown in FIG. 4, so that the magnets do not contact the surface but maintain the magnetic coupling necessary to support and align the inspecting portions 14 and 16 such that the inspecting portions move in concert with the actuating portion 12 during the inspection of the structure. Further embodiments of the inspection device 10 may include sets of rollers, skids, skis, or the like at any location to facilitate movement of the portions of the inspection device or may include surfaces or features to facilitate the movement of the portions.

FIG. 6 illustrates an actuating portion 112 of a second embodiment of the inspection device of the present invention. The inspecting portions of the second embodiment of the inspection device are not shown to better illustrate the features of the actuating portion 112. The actuating portion 112 includes a motorized drive wheel 170 that is rotated by a motor 172 to provide for motorized positioning of the actuating portion 112 and the corresponding inspecting portions. The motorized drive wheel 170 allows a technician to control the inspection device from a terminal connected to the actuating portion and the inspecting portions so that the inspection device may be remotely controlled to generate data from the inspection sensors that may be processed and displayed, such as by a processing element. Therefore, the inspection device with the actuating portion 112 of FIG. 6 may be moved without manual contact by the technician, as required by the inspection device 10 of FIGS. 1–5. The drive wheel 170 of FIG. 6 contacts the surface of the structure that the actuating portion 112 is placed upon and advantageously includes a textured surface to provide sufficient friction so that the drive wheel does not slip relative to the surface of the structure. A motor power supply (not shown) operated by a technician or with automated equipment provides power to the motor 172 to rotate the drive wheel 170 either forward or backward as required to perform the inspection.

The actuating portion 112 of the inspection device of FIG. 6 also includes a positional encoder device 174. The positional encoder device 174 advantageously provides position data for the inspection device for more accurate or informative inspection results. The positional encoder device 174, which may be mounted to the actuating portion 112, as illustrated in FIG. 6, or to one or more inspecting portions of alternative embodiments (not shown), sends a signal to a processing element indicating the position of the actuating portion 112, or the inspecting portions, which corresponds to the location of the inspection device. The positional encoder device 174 may measure the movement or location of the actuating portion and/or the inspecting portion(s) to which it is attached relative to any surface of the structure or relative to any frame of reference integral to the structure or independent of the structure being inspected. The processing element that advantageously receives the signal from the positional encoder device 174 may correlate the signal from the positional encoder device to the signals received from the inspection sensors so that any detected defects or flaws are accurately located on the structure. The positional encoder device 174 of FIG. 6 is an encoder wheel that produces a signal that corresponds to the rotation of the encoder wheel that contacts the surface that the actuating portion 112 is placed upon, which further corresponds to the location of the inspection device. Further embodiments of the present invention may include a positional encoder device that alternatively measures the movement and/or location of the inspection device, a non-limiting example being an optical encoder that optically measures movement of the inspection device, for more accurate or informative inspection results.

FIG. 7 illustrates a third embodiment of the inspection device 210 that includes a first inspecting portion 214 and second inspecting portion 216, each having a vertical array of inspection sensors 250 and 252, respectively. Vertical arrangement of the inspection sensors 250 and 252 provides for additional inspection data during a single inspection iteration and allows inspection of areas further removed from the actuating portion 212. Further embodiments of the inspection device may have arrays of inspection sensors in any arrangement. Non-limiting examples include the horizontal arrangement shown in FIG. 4 or the angled arrangement shown in FIG. 3. In addition, the inspection sensors may be located on the inspecting portion at any position relative to the magnets of the inspecting portion.

FIG. 8 illustrates a fourth embodiment of the inspection device 310 of the present invention. The inspection device 310 of FIG. 8 comprises only one inspecting portion 314 that further comprises at least one inspection sensor 350 to perform one-sided inspections as described above. In addition, the inspection sensors 350 of FIG. 8 comprise wireless data transmission either directly or indirectly to the processing element. Examples of such wireless data communication include, but are not limited to, WiFi applications, Bluetooth applications, or other wireless LAN applications known in the art.

The inspection device of the present invention provides many improvements to non-destructive inspection techniques. The inspection device permits the inspection of features having limited access that may be difficult for a technician to reach or access. Inspections may also be conducted with or without couplants or may be performed with a single inspection sensor or a plurality of sensors arranged in various configurations. In addition, the inspection device provides for one-sided inspections of features, which is particularly advantageous when the opposite side of the feature is inaccessible. Furthermore, the inspection device provides remote control for convenient operation by the technician and simplified processing and monitoring of the inspection data. Still further improvements to non-destructive inspection techniques apparent to one skilled in the art are also provided by the inspection device of the present invention.

Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A non-destructive inspection device for inspecting a feature of a structure, the inspection device comprising:
   an actuating portion having at least one magnet, wherein the actuating portion is structured for placement on a first surface of the structure such that the actuating portion is movable relative to the structure;
   a first inspecting portion having a first inspection sensor and at least one magnet, and
   a second inspecting portion having a second inspection sensor and at least one magnet,
   wherein the first and second inspecting portions are structured for positioning on a second surface of the structure opposite the first surface such that the feature of the structure to be inspected is located between the first and second inspecting portions, wherein the first and second inspecting portions are magnetically coupled to the actuating portion so that movement of the actuating portion causes the first and second inspecting portions to move in concert with the actuating portion without the first and second inspecting portions directly contacting the actuating portion, and wherein the first and second inspecting portions are in a generally fixed relative position with respect to each other when each is magnetically coupled to the actuating portion.

2. A non-destructive inspection device according to claim 1 wherein the inspection sensor of the first inspecting portion comprises an ultrasonic transmitter and the second inspection sensor of the second inspecting portion comprises an ultrasonic receiver.

3. A non-destructive inspection device according to claim 2 wherein the first inspecting portion includes an array of ultrasonic transmitters and the second inspecting portion includes an array of ultrasonic receivers.

4. A non-destructive inspection device according to claim 1 wherein the first inspecting portion includes a plurality of magnets, the second inspecting portion includes a plurality of magnets, and the actuating portion includes a first plurality of magnets magnetically coupled to the plurality of magnets of the first inspecting portion and includes a second plurality of magnets magnetically coupled to the plurality of magnets of the second inspecting portion.

5. A non-destructive inspection device according to claim 4 wherein the first inspecting portion includes a set of rollers proximate the plurality of magnets, the second inspecting portion includes a set of rollers proximate the plurality of magnets, and the actuating portion includes a set of rollers proximate the first plurality of magnets and the second plurality of magnets.

6. A non-destructive inspection device according to claim 5 wherein the actuating portion includes a handle for manual positioning of the actuating portion.

7. A non-destructive inspection device according to claim 5 wherein the actuating portion includes a motorized drive wheel for motorized positioning of the actuating portion.

8. A non-destructive inspection device according to claim 7 wherein the actuating portion includes a positional encoder device to monitor the positioning of the actuating portion.

9. A non-destructive inspection device according to claim 1 wherein the inspection sensor of the inspecting portion comprises an optical borescope.

10. A non-destructive inspection device for inspecting a feature of a structure, the inspection device comprising:
    an actuating portion having at least one magnet, wherein the actuating portion is structured for placement on a first surface of the structure such that the actuating portion is movable relative to the structure; and
    an inspecting portion having an inspection sensor and at least one magnet, wherein the inspecting portion is structured for positioning on a second surface of the structure opposite the first surface such that the inspecting portion is magnetically coupled to the actuating portion so that movement of the actuating portion causes the inspecting portion to move in concert with the actuating portion without the inspecting portion directly contacting the actuating portion, wherein the inspecting portion includes a positional encoder device to monitor the positioning of the actuating portion.

11. A non-destructive inspection device for inspecting a feature of a structure, the inspection device comprising:
    an actuating portion having at least one magnet, wherein the actuating portion is structured for placement on a first surface of the structure such that the actuating portion is movable relative to the structure; and an inspecting portion having an inspection sensor and at least one magnet, wherein the inspecting portion is structured for positioning on a second surface of the structure opposite the first surface such that the inspecting portion is magnetically coupled to the actuating portion so that movement of the actuating portion causes the inspecting portion to move in concert with the actuating portion without the inspecting portion directly contacting the actuating portion, wherein the inspection sensor of the inspecting portion comprises a laser ultrasonic transducer.

12. A non-destructive inspection device for inspecting a feature of a structure, the inspection device comprising:

an actuating portion having a first plurality of magnets and a second plurality of magnets, wherein the actuating portion is structured for placement on a first surface of the structure such that the actuating portion is movable relative to the structure;

a first inspecting portion having a first inspection sensor and a first plurality of magnets, wherein the first inspecting portion is structured for positioning on a surface of the structure opposite the first surface such that the first inspecting portion is magnetically coupled to the first plurality of magnets of the actuating portion so that movement of the actuating portion causes the first inspecting portion to move in concert with the actuating portion without the first inspecting portion directly contacting the actuating portion; and a second inspecting portion having a second inspection sensor and a second plurality of magnets, wherein the actuating portion has a second plurality of magnets such that the inspecting portion is structured for positioning on a surface of the structure opposite the first surface such that the feature of the structure to be inspected is located between the first inspecting portion and the second inspecting portion, wherein the second inspecting portion is magnetically coupled to the second plurality of magnets of the actuating portion so that movement of the actuating portion causes the second inspecting portion to move in concert with the actuating portion without the second inspecting portion directly contacting the actuating portion, and wherein the first inspecting portion and the second inspecting portion are in a generally fixed relative position with respect to each other when each is magnetically coupled to the actuating portion.

13. A non-destructive inspection device according to claim 12 wherein the first inspection sensor of the first inspecting portion comprises an ultrasonic transmitter and the second inspection sensor of the second inspecting portion comprises an ultrasonic receiver.

14. A non-destructive inspection device according to claim 13 wherein the first inspecting portion includes an array of ultrasonic transmitters and the second inspecting portion includes an array of ultrasonic receivers.

15. A non-destructive inspection device according to claim 14 wherein the actuating portion includes a handle for manual positioning of the actuating portion.

16. A non-destructive inspection device according to claim 14 wherein the actuating portion includes a motorized drive wheel for motorized positioning of the actuating portion.

17. A non-destructive inspection device according to claim 16 wherein the actuating portion includes a positional encoder device to monitor the positioning of the actuating portion.

18. A non-destructive inspection device according to claim 12 wherein at least one inspecting portion includes a positional encoder device to monitor the positioning of the inspecting portion.

19. A method of inspecting a feature of a structure, comprising the steps of:

placing an actuating portion of a non-destructive inspection device on a first surface of the structure, wherein the actuating portion has at least one magnet;

positioning first and second inspecting portions of the non-destructive inspection device on a second surface of the structure opposite the first surface such that the feature of the structure to be inspected is located between the first and second inspecting portions, wherein the first and second inspecting portions each have an inspection sensor and at least one magnet such that positioning the first and second inspecting portions comprises magnetically coupling the magnet of the actuating portion to the magnets of the first and second inspecting portions;

moving the actuating portion on the first surface of the structure such that the first and second inspecting portions are moved in concert with the actuating portion; and monitoring an output from the inspection sensor of at least one of the first and second inspecting portions.

20. A method according to claim 19, further comprising the steps of:

transmitting an ultrasonic signal from the first inspection sensor through the feature of the structure to be inspected; and receiving the ultrasonic signal in the second inspection sensor to generate the output to be monitored.

21. A non-destructive inspection device for inspecting a feature of a structure, the inspection device comprising:

an actuating portion having at least one magnet, wherein the actuating portion is structured for placement on a first surface of the structure such that the actuating portion is movable relative to the structure; and an inspecting portion having an inspection sensor and at least one magnet, wherein the inspecting portion is structured for positioning on a second surface of the structure opposite the first surface such that the inspecting portion is magnetically coupled to the actuating portion so that movement of the actuating portion causes the inspecting portion to move in concert with the actuating portion without the inspecting portion directly contacting the actuating portion, wherein the feature of the structure extends from the second surface of the structure and wherein the inspecting portion is further structured for inspecting the feature of the structure extending from the second surface of the structure.

22. A method of inspecting a feature of a structure, comprising:

placing an actuating portion of a non-destructive inspection device on a first surface of the structure, wherein the actuating portion has at least one magnet;

positioning at least one inspecting portion of the non-destructive inspection device on a second surface of the structure opposite the first surface, wherein the inspecting portion has an inspection sensor and at least one magnet such that positioning the inspecting portion comprises magnetically coupling the magnet of the actuating portion to the magnet of the inspecting portion;

moving the actuating portion on the first surface of the structure such that the inspecting portion is moved in concert with the actuating portion, wherein the feature of the structure extends from the second surface of the structure and wherein moving the actuating portion further comprises moving the actuating portion such that the inspecting portion inspects the feature of the structure extending from the second surface of the structure; and monitoring an output from the inspection sensor.

* * * * *